United States Patent
Bhave et al.

(10) Patent No.: US 9,932,648 B2
(45) Date of Patent: Apr. 3, 2018

(54) FLOW-THROUGH PRETREATMENT OF LIGNOCELLULOSIC BIOMASS WITH INORGANIC NANOPOROUS MEMBRANES

(71) Applicants: UT-Battelle, LLC, Oak Ridge, TN (US); Trustees of Dartmouth College, Hanover, NH (US)

(72) Inventors: Ramesh R. Bhave, Knoxville, TN (US); Lee Lynd, Meriden, NH (US); Xiongjun Shao, White River Junction, VT (US)

(73) Assignee: UT-Battelle, LLC, Oak Ridge, TN (US)

( * ) Notice: Subject to any disclaimer, the term of this patent is extended or adjusted under 35 U.S.C. 154(b) by 54 days.

(21) Appl. No.: 14/354,230

(22) PCT Filed: Oct. 30, 2012

(86) PCT No.: PCT/US2012/062520
§ 371 (c)(1),
(2) Date: Apr. 25, 2014

(87) PCT Pub. No.: WO2013/066842
PCT Pub. Date: May 10, 2013

(65) Prior Publication Data
US 2014/0318532 A1 Oct. 30, 2014

Related U.S. Application Data

(60) Provisional application No. 61/553,424, filed on Oct. 31, 2011.

(51) Int. Cl.
*C13K 1/02* (2006.01)
*C13K 1/04* (2006.01)
(Continued)

(52) U.S. Cl.
CPC .............. *C13K 1/02* (2013.01); *B01D 61/027* (2013.01); *B01D 71/024* (2013.01); *C13K 1/04* (2013.01); *C12P 2201/00* (2013.01)

(58) Field of Classification Search
CPC ........................................................ C13K 1/02
See application file for complete search history.

(56) References Cited

U.S. PATENT DOCUMENTS

| 4,981,590 A | 1/1991 | Van 'T Veen et al. |
| 5,028,336 A * | 7/1991 | Bartels ................ B01D 61/027 210/639 |

(Continued)

FOREIGN PATENT DOCUMENTS

| JP | 2011-205987 | 10/2011 |
| JP | 2011205987 A | 10/2011 |

(Continued)

OTHER PUBLICATIONS

Machine translation of WO98/17378 downloaded on Mar. 27, 2017.*

(Continued)

*Primary Examiner* — Douglas B Call
(74) *Attorney, Agent, or Firm* — Warner Norcross & Judd, LLP

(57) ABSTRACT

A process for the pretreatment of lignocellulosic biomass is provided. The process generally includes flowing water through a pretreatment reactor containing a bed of particulate ligno-cellulosic biomass to produce a pressurized, high-temperature hydrolyzate exit stream, separating solubilized compounds from the hydrolyzate exit stream using an inorganic nanoporous membrane element, fractionating the retentate enriched in solubilized organic components and recycling the permeate to the pretreatment reactor. The pretreatment process provides solubilized organics in con- (Continued)

centrated form for the subsequent conversion into biofuels and other chemicals.

8 Claims, 10 Drawing Sheets

(51) Int. Cl.
*B01D 61/02* (2006.01)
*B01D 71/02* (2006.01)

(56) References Cited

U.S. PATENT DOCUMENTS

| | | |
|---|---|---|
| 6,991,737 B2 | 1/2006 | Oyachi et al. |
| 7,226,657 B1 | 6/2007 | Delmotte et al. |
| 2004/0076874 A1 | 4/2004 | Nickel et al. |
| 2004/0116275 A1 | 6/2004 | Benfer et al. |
| 2006/0175256 A1 | 8/2006 | Masten et al. |
| 2009/0061495 A1* | 3/2009 | Beatty ............... C12P 7/10 435/165 |
| 2009/0270609 A1* | 10/2009 | Heikkila ............ C13B 20/165 536/127 |
| 2010/0056369 A1* | 3/2010 | Gu ................... B01D 63/066 502/402 |
| 2011/0025306 A1 | 2/2011 | Ackermann et al. |
| 2011/0077446 A1 | 3/2011 | Shanbhag et al. |
| 2011/0192075 A1 | 8/2011 | Kale |
| 2011/0287215 A1* | 11/2011 | Bishop ............. B01D 67/0058 428/131 |
| 2012/0115192 A1* | 5/2012 | Lali ................. C12P 19/14 435/100 |

FOREIGN PATENT DOCUMENTS

| | | | |
|---|---|---|---|
| WO | WO98/17378 | * | 4/1998 |
| WO | 2006/022719 | | 3/2006 |
| WO | 2008/141413 | | 11/2008 |
| WO | WO 2010/137039 | * | 12/2010 |
| WO | WO 2011/163137 | * | 12/2011 |

OTHER PUBLICATIONS

International Search Report and Written Opinion of the International Searching Authority for International Application No. PCT/US2012/062520 dated Jan. 17, 2013.

* cited by examiner

CARBOHYDRATE RETENTION: POPLAR
(2.5 NM TITANIA; 185-215° C; 300-500 PSI)

| SAMPLE | GLUCOSE g/L | XYLOSE g/L | ARABINOSE g/L | % RETENTION GLUCOSE | % RETENTION XYLOSE | % RETENTION ARABINOSE |
|---|---|---|---|---|---|---|
| FEED | 0.197 | 1.556 | 0.102 | - | - | - |
| PERMEATE | 0.003 | 0.041 | 0.001 | 98.5 | 97.4 | 99 |
| PERMEATE | 0.001 | 0.017 | 0 | 99.5 | 98.9 | 100 |
| PERMEATE | 0 | 0.015 | 0 | 100 | 100 | 100 |
| RETENTATE | 0.241 | 1.891 | 0.122 | - | - | - |

Fig. 8

CARBOHYDRATE RETENTION: BAGASSE
(2.5 NM TITANIA, 190-205° C; 300-450 PSI)

| SAMPLE | GLUCOSE g/L | XYLOSE g/L | ARABINOSE g/L | % RETENTION GLUCOSE | % RETENTION XYLOSE | % RETENTION ARABINOSE |
|---|---|---|---|---|---|---|
| FEED | 0.261 | 2.131 | 0.19 | - | - | - |
| PERMEATE | 0.001 | 0.027 | 0.002 | 99.4 | 98.7 | 98.9 |
| PERMEATE | 0.001 | 0.031 | 0.006 | 99.4 | 98.5 | 96.9 |
| PERMEATE | 0 | 0.019 | 0.006 | 100 | 99.2 | 97.5 |
| RETENTATE | 0.284 | 2.497 | 0.237 | - | - | - |

FLOW-THROUGH PRETREATMENT OF LIGNOCELLULOSIC BIOMASS WITH INORGANIC NANOPOROUS MEMBRANES

This invention was made with government support under Contract No. DE-AC05-00OR22725 awarded by the U.S. Department of Energy. The government has certain rights in the invention.

STATEMENT OF JOINT RESEARCH AGREEMENT

The invention was made pursuant to a joint research agreement between Oak Ridge National Laboratory and Dartmouth College that was in effect on or before the date the claimed invention was made, and as a result of activities undertaken within the scope of the joint research agreement.

BACKGROUND OF THE INVENTION

The present invention relates to a process for the pretreatment of lignocellulosic feedstocks.

Lignocellulosic feedstocks have been proposed as an alternative fuel source for the production of bio-ethanol and other chemicals. Exemplary feedstocks include corn stover, bagasse, switchgrass, pine and poplar. However, these feedstocks typically require pretreatment to overcome their inherent recalcitrance to attack by microorganisms and their enzymes. Existing methods of pretreatment include flow-through pretreatment and steam pretreatment. Flow-through pretreatment includes directing water through a bed of lignocellulosic feedstock. This method optionally includes the addition of mineral acids to promote hydrolysis of the feedstocks into fermentable sugars. Steam pretreatment, by comparison, demonstrates lower material costs over flow-through methods while enhancing the reactivity of the resulting solids.

Despite their advantages, known pretreatment methods involve the partial thermochemical depolymerization and degradation of carbohydrates and lignins in the feedstock. In particular, known flow-through and steam pretreatment methods include sugar losses and yield compounds inhibitory to fermentation. Accordingly, there remains a continued need for an improved pretreatment method to leverage the benefits of lignocellulosic feedstock as a potential fuel source. In addition, there remains a continued need for a system that can retain carbohydrates and lignins at pretreatment conditions while producing a superior concentrate of reactive organics.

SUMMARY OF THE INVENTION

A process for the pretreatment of lignocellulosic biomass is provided. The process generally includes flowing water through a pretreatment reactor containing a bed of particulate lignocellulosic biomass to produce a pressurized, high-temperature hydrolyzate exit stream, separating solubilized compounds from the hydrolyzate exit stream using an inorganic nanoporous membrane element, fractionating the retentate enriched in solubilized organic components and recycling the permeate to the pretreatment reactor.

In one embodiment, the hydrolyzate exit stream is directed through the inorganic nanoporous membrane at temperatures between 170° C. and 230° C. When a pressure differential sufficient to maintain solubilized compounds in the liquid phase is applied across the membrane, solvents are forced through the nanoporous membrane element while the solutes are largely rejected. The size of the solutes excluded in this separation are on the order of one nanometer and can include a molecular weight of less than 200 Da. The solvent-rich permeate is then recycled to the pretreatment reactor, and the retentate is thereafter fractionated and fermented to produce ethanol, for example.

In another embodiment, the nanoporous membrane element used in the separation of low molecular weight organics includes a tubular structure having an inner separating layer, an outer supporting layer, and at least one intermediate layer. In this embodiment, the separating layer is nanoporous to selectively retain solubilized organics while permitting the transfer of high-temperature solvents therethrough. The layers can form a single- or multi-channel composite structure in which a sieving separation mechanism allows solvents to permeate radially through the inorganic membrane.

These and other features and advantages of the present invention will become apparent from the following description of the invention, when viewed in accordance with the accompanying drawings and appended claims.

BRIEF DESCRIPTION OF THE DRAWINGS

FIG. 8 is a table illustrating carbohydrate retention for poplar feedstock.

FIG. 9 is a table illustrating carbohydrate retention for bagasse feedstock.

DETAILED DESCRIPTION OF THE CURRENT EMBODIMENTS

The invention as contemplated and disclosed herein includes an inorganic nanoporous membrane element and a method for the pretreatment of lignocellulosic biomass utilizing the nanoporous membrane element to separate low molecular weight solubilized organics at high temperatures and pressures (to maintain the solubilized fractions are in liquid form) for conversion into bio-fuels and for other applications.

I. Nanoporous Membrane

Figure 1:
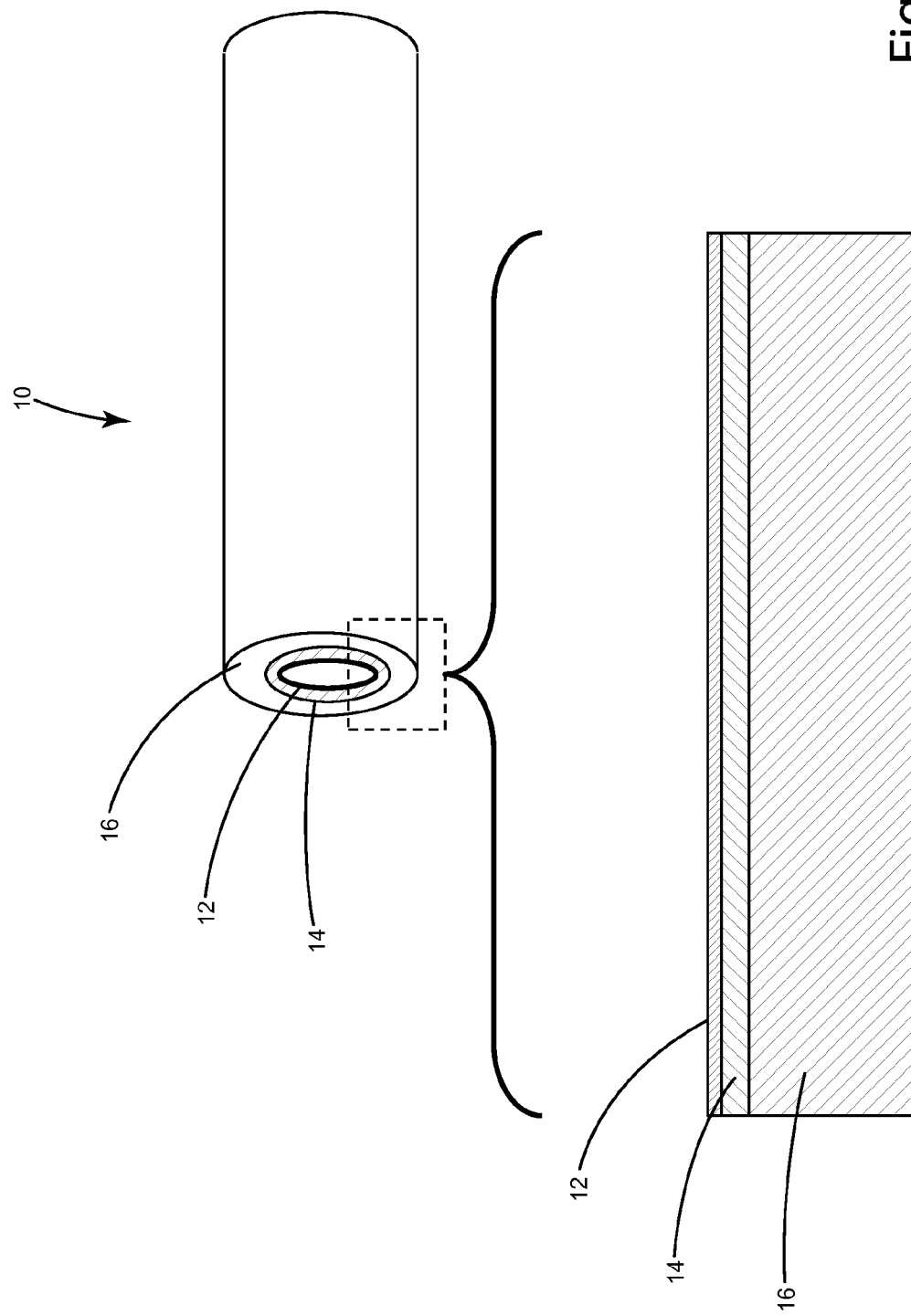
FIG. 1 is a diagram of an inorganic nanoporous membrane element in accordance with the present invention.

A nanoporous membrane element in accordance with an embodiment of the invention is illustrated in FIG. 1 and generally designated 10. The nanoporous membrane element 10 of the present embodiment includes a single- or multi-channel structure having an inner separating layer 12, an outer supporting layer 16, and at least one intermediate layer 14 interposed between the separating and supporting layers, where the separating layer 12 is nanoporous to selectively retain low organic weight solutes while permitting the transfer of high temperature solvents through the membrane.

The inner nanoporous separating layer 12 includes a mean pore size selected to retain solutes having a molecular weight as low as a few hundred Daltons. In the present embodiment, the mean pore size is between 0.5 nm and 2 nm, while in other embodiments the mean pore size can vary outside of this range, including for example 2 nm, 4 nm, 5 nm or 10 nm. The separating layer 12 includes a thickness of less than 1 micron up to approximately 10 microns, and can be formed from a suitable ceramic, including metal oxides such as alumina, titania, silica and zirconia, as well as carbon.

The intermediate layer 14 includes an intermediate pore size to ensure the separative layer 12 does not fill the larger pores of the supporting layer 16 and thereby degrade membrane permeability. In one embodiment, the intermediate layer 14 defines a mean pore size of approximately 0.1 to 1.0 microns, which is less than the mean pore size of the supporting layer 16, but greater than the mean pore size of the separating layer 12. While only one intermediate layer 14 is shown in FIG. 1, the membrane 10 can include two or more intermediate layers each having a stepped increase in pore size over the adjacent inner intermediate layer. Where a single intermediate layer 14 is used as shown in FIG. 1, the intermediate layer can have a thickness of between 10 microns to 100 microns, again depending on the material utilized. Suitable materials include, but are not limited to, ceramics such as alumina, titania, silica and zirconia, as well as silicon carbide and carbon for example.

The outer supporting layer 16 provides mechanical strength to withstand an outward pressure differential applied across the membrane element 10. Depending on the pressure differential and the supporting layer material, the supporting layer 16 can have a thickness generally between 0.5 mm and 5 mm. The supporting layer 16 can be formed of any suitably strong porous material, including porous metal such as stainless steel and nickel, carbon, silicon carbide or a metal oxide such as alumina, titania, silica and zirconia. The mean pore size for the supporting layer typically differs from the separating layer pore size by an order of magnitude or more. For example, the supporting layer pore size can be approximately 2 to 10 microns in the illustrated embodiment, or roughly three to four orders of magnitude greater than the nanoporous pore size of the separating layer 12. This type of composite microstructure has the potential to offer the optimal membrane permeability, which can be an important factor to maximize overall throughput and process yield.

Figure 2:
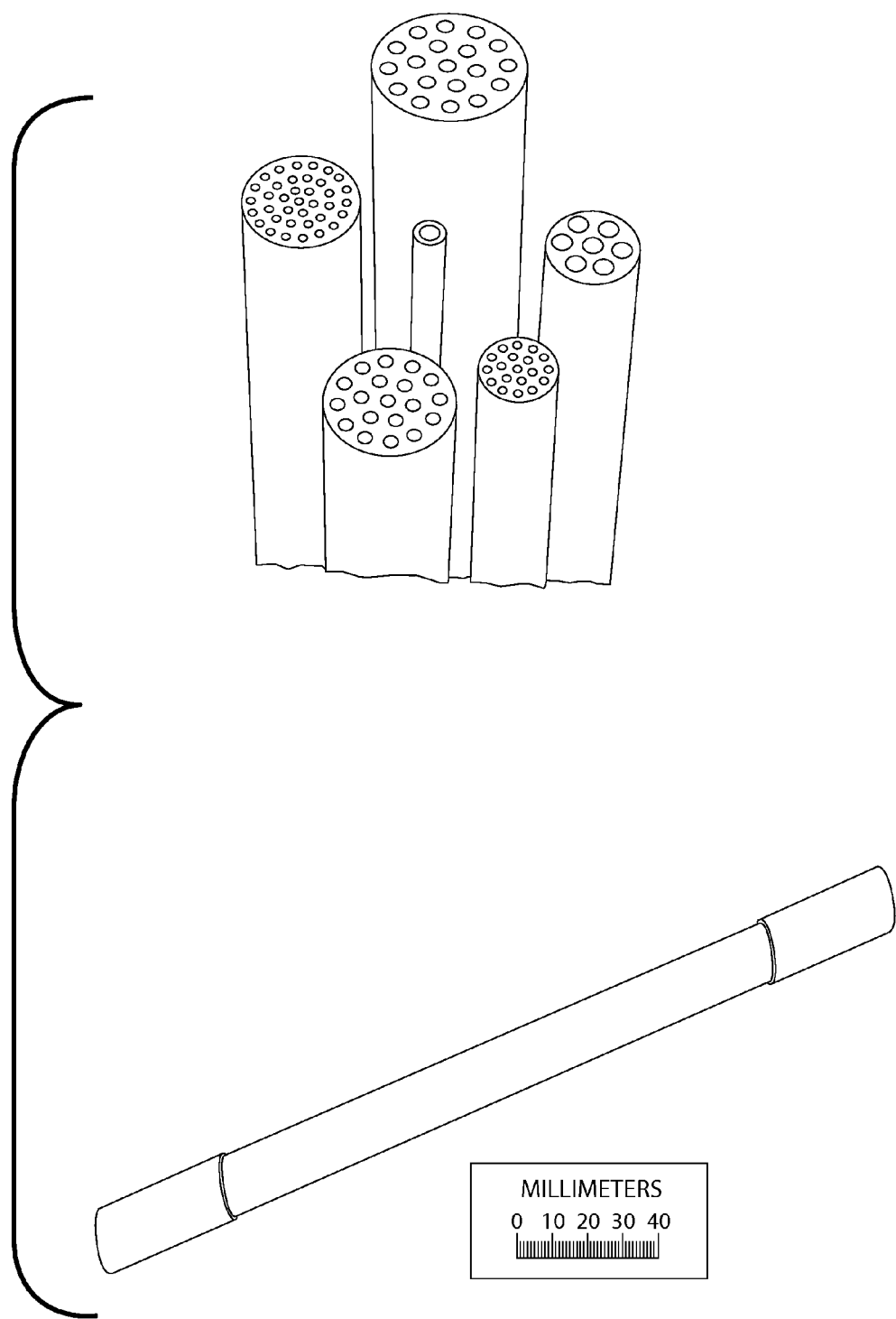
FIG. 2 are perspective and elevational views of single- and multi-channel inorganic nanoporous membrane elements in accordance with the present invention.

Each layer can be formed according to conventional methods and subsequently thermally bonded to its adjoining layer to form a tubular single- or multi-channel composite structure. In a single-channel membrane as shown in FIG. 1, the outer diameter can be approximately 10 to 12mm, and the channel diameter can be approximately 7 to 10 mm. In a multi-channel configuration as shown in FIG. 2, each channel can have a diameter of between 1 and 6 mm. These dimensions can vary from application to application however, and can include diameters outside the above ranges if desired for the particular application. In addition, other geometries are possible, including planar multi-layer membranes for example.

During use, a solution is directed through the one or more channels in the nanoporous membrane element 10. If the transmembrane pressure, i.e. the pressure differential applied across the membrane 10 element, is sufficient to overcome the minimum pressure required to keep all feed components in the liquid phase (i.e. prevents volatilization of water and some of the solubilized feed constituents), the solvent permeates through the nanoporous layer 12 while solutes are prevented from permeating through the nanoporous layer. The mechanism of transport across the membrane element 10 is a sieving action, which differs from reverse osmosis, in which the solute must first solubilize in a dense separating layer and then diffuse across the membrane. Thus, the nanoporous membrane 10 is superior to reserve osmosis membranes in many applications because it is not limited by diffusability and solubility considerations.

Typical pressure differentials for the nanoporous membrane element 10 include 200 psig to 550 psig. These values depend on feed characteristics and make separations possible in the liquid phase, preventing vaporization of volatile constituents in the pretreatment process. This pressure differential is significantly less than the pressure differential applied in reverse osmosis membranes, for example, which can require pressure differentials of greater than 1000 psig to overcome low diffusivity and solubility through a dense separating layer and to provide for reasonable flux for industrial scale processing. In addition, the nanoporous membrane element 10 is less prone to fouling when compared to reverse osmosis membranes. The sugars or lignins that clog the pores in the nanoporous separating layer 12 can be dissolved with the application of dilute solution (<1 wt. %) of sodium hydroxide for example. In reverse osmosis membranes, however, the caustic or acid chemical (depending on the solutes) cannot easily permeate through the fouled dense separating layer and thereby may not regenerate efficiently for long term use due to the substantially lowered permeability of the reverse osmosis membrane due to fouling under process conditions.

II. Pretreatment Process

A Flow-Through Recycle (FTR) process for the pretreatment of lignocellulosic biomass is provided, in which the inorganic nanoporous membrane element 10 is utilized to separate low molecular weight organics at high temperatures. The FTR process generally includes flowing water through a pretreatment reactor containing a bed of particulate lignocellulosic biomass, separating solubilized compounds from the reactor using the inorganic nanoporous membrane element, removing retentate fractions enriched in solubilized organic components, and recycling water to the pretreatment reactor.

Figure 3:
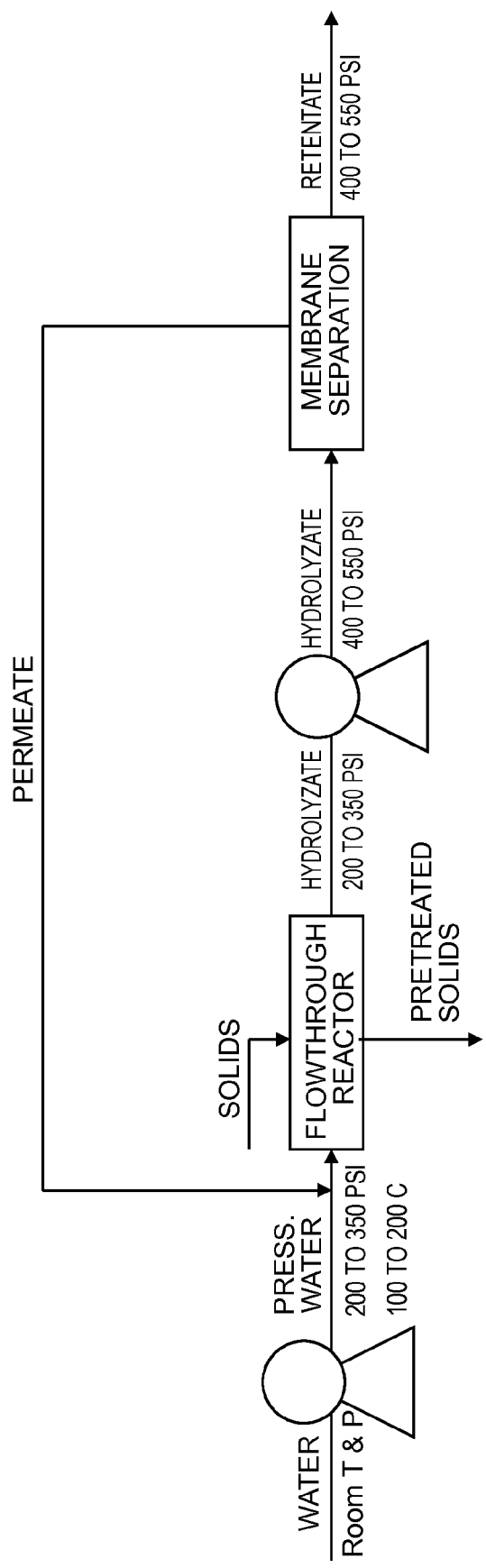
FIG. 3 is a first flow diagram of the pretreatment process of the present invention utilizing the inorganic membrane element of FIG. 1.

More specifically, and with reference to FIG. 3, a biomass substrate is first suspended in a flow-through reactor. The biomass can include, but is not limited to, corn stover, bagasse, switchgrass, poplar, pine and combinations thereof. The reactor chamber is then heated to between 180° C. and 230° C. for a predetermined period, for example between 12 to 20 minutes, followed by the introduction of pressurized water heated to between 170° C. and 210° C. to create a hydrolyzate exit stream. The reactor chamber can be heated to other temperatures as desired, and the water temperature can be varied as well. In some applications, the pretreatment process can optionally include one or more dilute acid treatments to promote hydrolysis of the feedstocks into fermentable compounds. In the present embodiment, however, no acid treatments are utilized.

The hydrolyzate exit stream contains solubilized organics including diluted amounts of reactive solids from the pretreatment reactor. For example, the reactive solids can include glucose, xylose, pentose, lignin, oligo and polysaccharides from the lignocellulosic biomass. The hydrolyzate exit stream is then pressurized to between 200 psi and 550 psi before membrane separation, during which time its mean temperature can remain up to 230° C. depending on the maximum operating pressure to perform the desired separation and fractionation in the liquid phase. The pressurized hydrolyzate stream is then directed through the one or more channels in a nanoporous inorganic membrane element to generate a retentate having an increased concentration of reactive solids. When high pressure sufficient to produce acceptable flux under liquid phase conditions is applied to the feed side of the membrane element, water is forced through the nanoporous structure of the membrane surface while the solutes are largely rejected. During this separation, the hydrolyzate exit stream is at or near the pretreatment reaction temperature and pressure. The size of the solutes excluded in this separation are on the order of one nanometer. The driving force of the separation process is the pressure difference between the retentate and the permeate side at the separation layer 12 of the membrane 10. The permeate is then recycled to the flow-through reactor as shown in FIG. 3, and the retentate (enriched in sugars) is thereafter fractionated and fermented to produce ethanol, for example.

Figure 4:
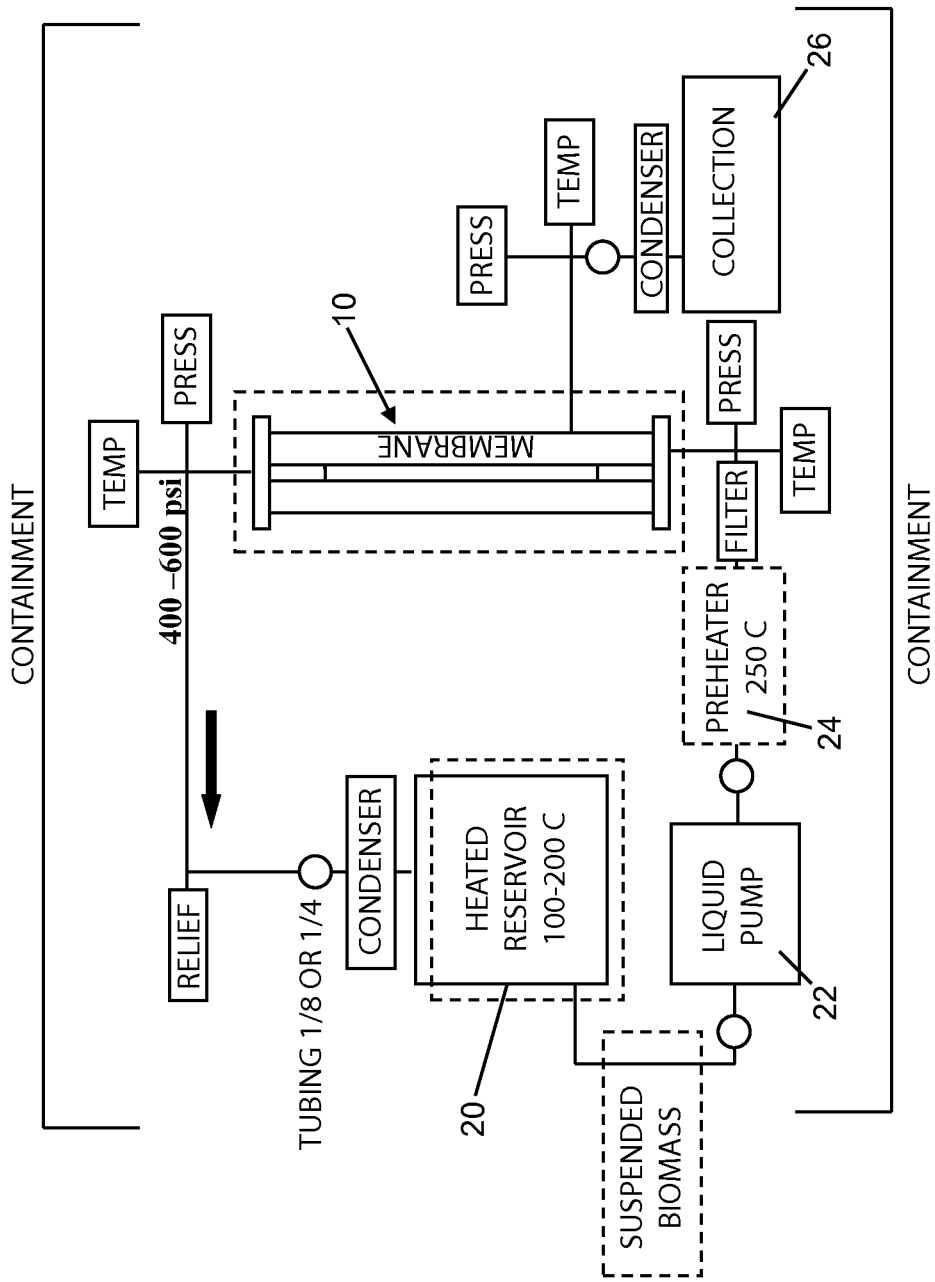
FIG. 4 is a second flow diagram of the pretreatment process of the present invention utilizing the inorganic membrane element of FIG. 1

The FTR pretreatment process can also include a recirculation of the retentate. Referring now to FIG. 4, the water supply is first pressurized and heated within a reservoir 20 to between 100° C. and 200° C. Pressurized water from the reservoir 20 is directed through the suspended lignocellulosic biomass and then through a high temperature pump 22 and a preheater 24. The resulting high temperature, high pressure biomass hydrolyzate is directed through a channel defined in the inorganic membrane element 10. The permeate is collected at a collection reservoir 26 while the retentate is recirculated to the heated reservoir 20. In this configuration, no chemicals (other then water) are added to prepare the hydrolyzate of the biomass suspension. For example, this configuration does not include the addition of an acid or a base to the biomass suspension, which might otherwise convert certain organic solutes into products that are inhibitory to fermentation. The configuration as shown in FIG. 4 can also be utilized to clean the membrane element 10 of fouling, in which a caustic solution is utilized in place of the biomass hydrolyzate. If caustic solutions are not utilized, foulants can also be removed with the application of high temperature steam to membrane element 10.

To reiterate, separation of the retentate is performed at high temperatures which minimize the impact of carbohydrate and lignin degradation while providing a clean sugar stream. The use of inorganic nanoporous membranes is advantageous over widely used polymeric membranes, which are temperature limited to substantially less than 100° C. The use of inorganic nanoporous membranes is also advantageous over reverse osmosis membranes, which are typically operated at higher pressures (>1000 psig) to overcome the physical resistance of a dense membrane (due to the low diffusivity and solubility of the solutes), and which are more prone to fouling. In addition, the inorganic nanoporous membrane element 10 provides increased flux, separation and ease of regeneration, while also selectively retaining sugars, lignin and proteins and recycling water back to the pretreatment reactor.

Figure 5:
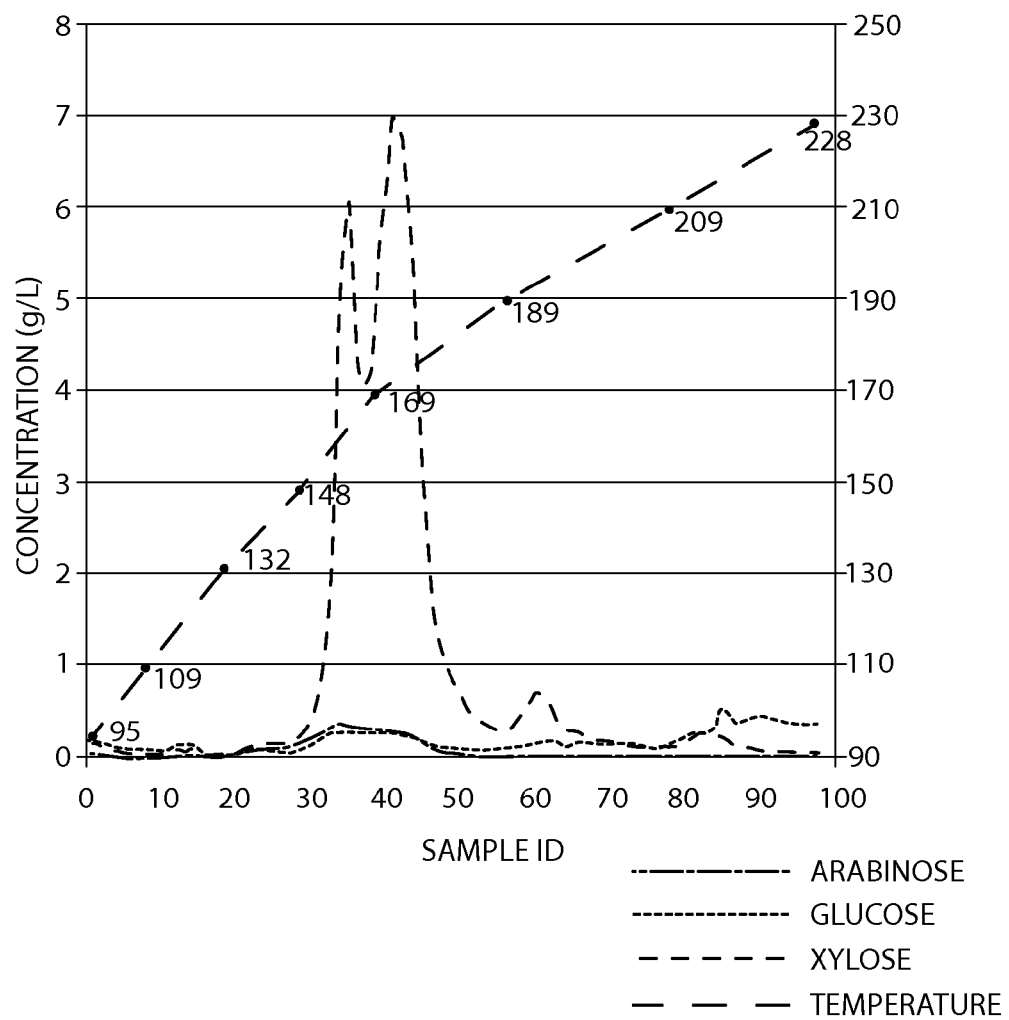
FIG. 5 is a graph of illustrating the stepwise fractionation of carbohydrate fractions at different temperatures during membrane pretreatment.

The FTR pretreatment method of the present invention can achieve highly reactive solids, minimal formation of sugar degradation products, a non-inhibitory hydrolyzate, reasonable energy requirements, and fractionation and recovery of solubilized biomass components in concentrated form. Laboratory testing confirmed the effectiveness of the nanoporous membrane element 10 in retaining select carbohydrates in the hydrolyzate feed. Carbohydrate retention was evaluated for both poplar and bagasse according to the following formula: % retention=(g/L in feed−g/L in permeate)/(g/L in feed). During testing, the feed side pressure was maintained at 300 psi to 450 psi while the permeate side pressure was maintained at 100 psi to 350 psi. The feed flow rate was 15 ml/min, and the permeate flow rate was initially 3 ml/min, transitioning to 1 ml/min over a 30-40 min run. The contact time of the biomass hydrolyzate with the membrane was limited to less than 10 minutes to minimize the potential for sugar degradation at high temperatures. The carbohydrate retention rate for poplar at the start of the test run was determined to be 98.5% (glucose) and 97.4% (xylose), and the carbohydrate retention rate for bagasse was determined to be 99.4% (glucose) and 98.7% (xylose). At the end of the run the retention rates improved to 100% for poplar-glucose, poplar-xylose and bagasse-glucose and 99.2% for bagasse xylose. The water recovery was 15%-20%, and the permeate also showed partial removal (10-50%) of inhibitors such as 2-furfural which would help enhance reactivity and achieve a higher ethanol yield. With the use of a larger area module, combined with an increase in average permeate flux to greater than 50 liter/hr-m$^2$, water recovery can improve to between 50% and 80%. Additional laboratory testing confirmed the reactivity of select carbohydrates in the high-temperature retentate using a bagasse biomass. These results are shown in FIG. 5 with overall fractions of carbohydrates (arabinose, glucose and xylose) released at different temperatures.

Figure 6:
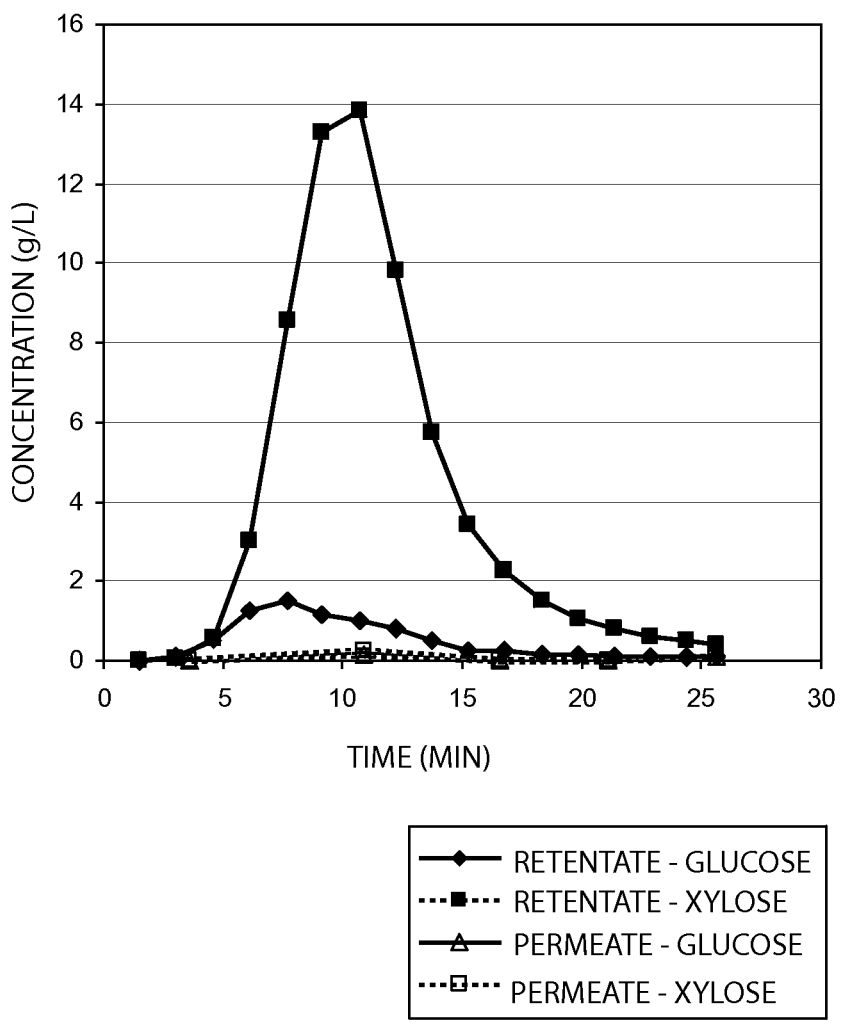
FIG. 6 is a graph illustrating corn stover carbohydrate concentrations.
Figure 7:
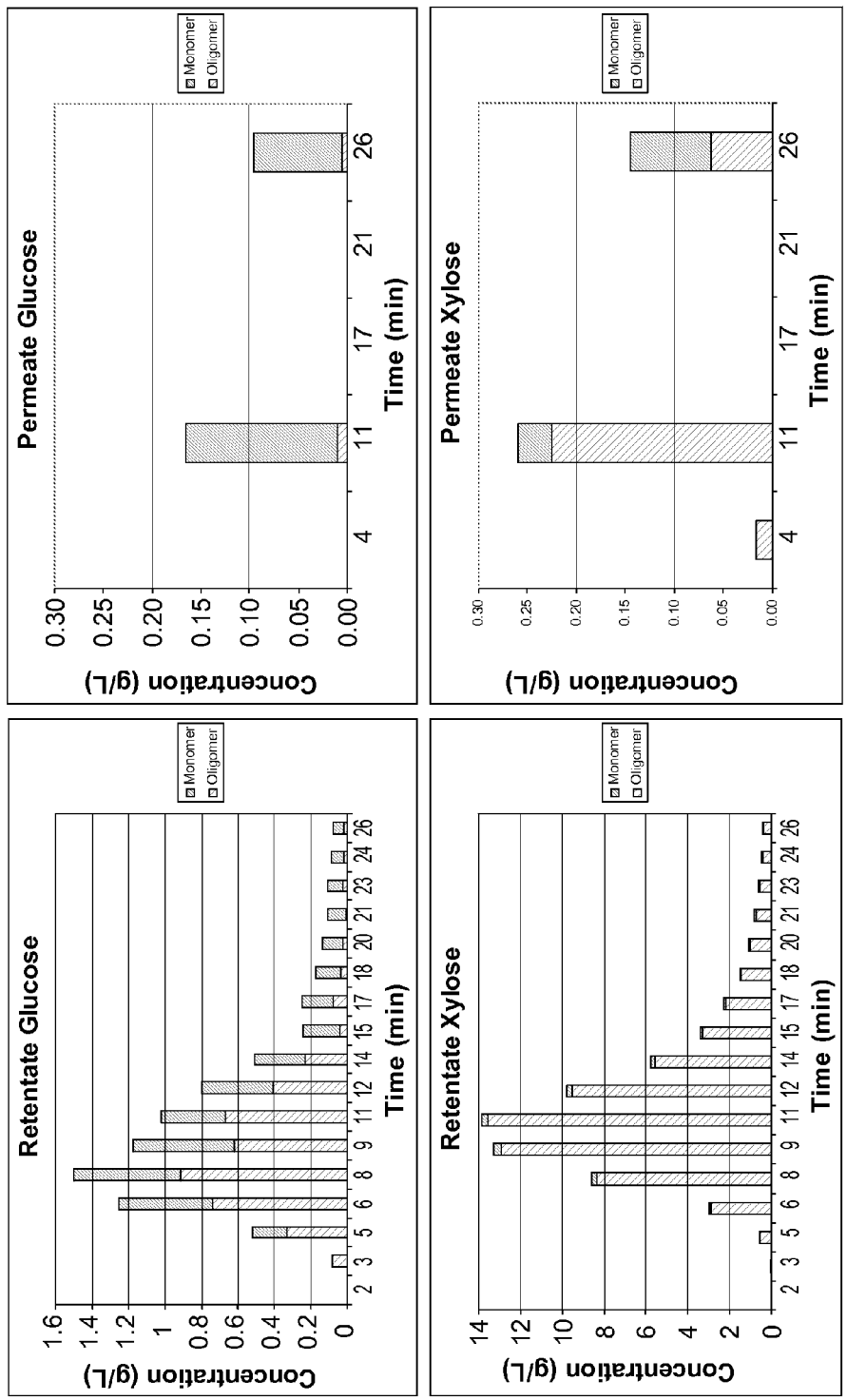
FIG. 7 are graphs illustrating corn stover carbohydrate concentrations including oligomers and monomers.

Additional laboratory testing confirmed the membrane's excellent retention of corn stover carbohydrates in a hydrolyzate feed at 180° C. to 190° C. at 200 psig with a 30 ml/min flow rate. The separation resulted in a retentate flow rate of 26.9 ml/min and a permeate flow rate of 3.1 ml/min. For a single pass process, 10.3% of the volume of the hydrolyzate feed transfers across the membrane 10 to form the permeate. FIG. 6 depicts the total glucose and xylose concentration in the retentate and permeate during the 26 minute test run. The percent of glucose/xylose in the permeate was 1.52% for glucose and 0.31% for xylose. The permeate xylose was predominantly oligomer as shown in FIG. 7, and the permeate glucose was approximately fifty percent monomer as also shown in FIG. 7.

FIGS. 8-9 are graphs illustrating the retention of select carbohydrates in laboratory testing of a membrane having a nanoporous titania separating layer with a mean pore size of 2.5 nm. In one evaluation, poplar hydrolyzate feed was heated to between 185° C. and 215° C. and pressurized to between 300 psig and 500 psig. The glucose retention was above 98%, the xylose retention was above 97% and the arabinose retention was at or above 99%. In another evaluation, bagasse hydrolyzate feed was heated to between 190° C. and 205° C. and pressurized to between 300 psig and 450 psig. The glucose retention was above 99%, the xylose retention was above 97% and the arabinose retention was at or above 96%, thereby increasing the carbohydrate retention by 15% to 20%. These results show nearly quantitative retention of carbohydrates with nanoporous inorganic membrane at pretreatment conditions. The reactivity of the concentrated carbohydrates were subsequently tested in *C. thermocellum* fermentation using a commercial cellulase, revealing a ~80% glucan conversion on poplar and a ~90% glucan conversion on bagasse. This represents a 15-20% increase over glucan conversion obtained using the conventional batch process.

Figure 10:
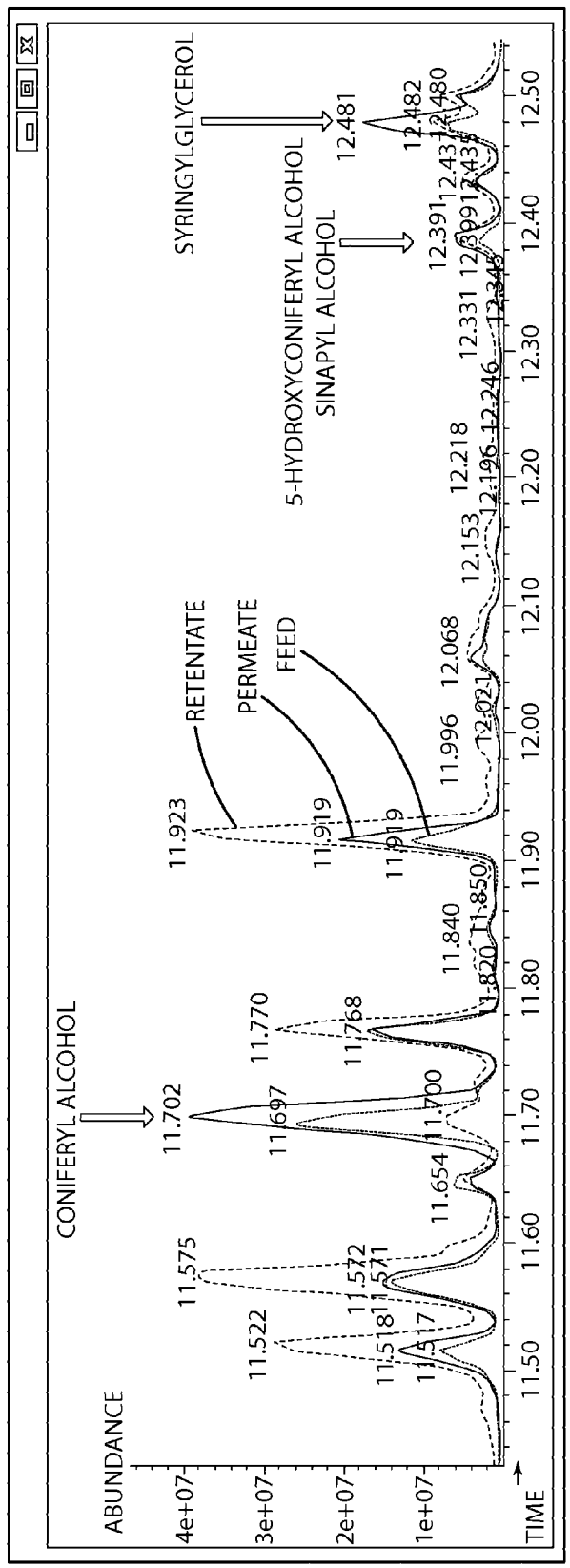
FIG. 10 is a GC-MS chart illustrating the separation and preferential permeation or removal of inhibitors.

As noted above, the hydrolyzate feed can contain low molecular weight organics that potentially inhibit the downstream fermentation of a fractionated retentate. These inhibitors can include monolignols formed in the breakdown of lignin and can also include phenolic acids/aldehydes. FIG. 10 is a Gas Chromatography-Mass Spectrometry (GC-MS) chart illustrating the removal of inhibitors from a bagasse hydrolyzate feed. As shown in FIG. 10, coniferyl alcohol (a monolignol) demonstrated a lowered concentration in the retentate relative to the feed and demonstrated a corresponding increase in concentration in the permeate. Sinapyl alcohol (a monolignol) and syringylglycerol (an aldehyde) also demonstrated a relative decrease in concentration in the retentate relative to the feed and demonstrated a corresponding increase in concentration in the permeate. The remaining peaks in FIG. 10 illustrate the desired retention of low molecular weight sugars in the bagasse retentate. Thus, the inorganic membrane 10 demonstrated the transfer of known inhibitors to the permeate while retaining desired low molecular weight organics for subsequent fractionation and fermentation into bio-fuels or other chemicals.

The above description is that of current embodiments of the invention. Various alterations and changes can be made without departing from the spirit and broader aspects of the invention as defined in the appended claims, which are to be interpreted in accordance with the principles of patent law including the doctrine of equivalents. Any reference to elements in the singular, for example, using the articles "a," "an," "the," or "said," is not to be construed as limiting the element to the singular.

The invention claimed is:

1. A pretreatment process comprising:
   passing a pressurized liquid through a lignocellulosic biomass to produce a pressurized solution containing solubilized glucose or solubilized xylose;
   directing the pressurized solution through a channel defined in an inorganic membrane element, the inorganic membrane element being adapted to separate the solubilized glucose or solubilized xylose from the pressurized liquid such that a permeate of the inorganic membrane element is substantially free of the solubilized glucose or solubilized xylose, the inorganic membrane element including:
   a nanoporous separating layer,
   a porous support defining a mean pore size of between 2.0 μm and 10.0 μm, and
   a porous intermediate layer interposed therebetween and bonded to the porous support and to the nanoporous separating layer, the porous intermediate layer defining a mean pore size of between 0.1 μm and 1.0 μm,
   wherein the nanoporous separating layer defines a mean pore size of between 0.5 nm and 2.0 nm to retain a substantial portion of the solubilized glucose or solubilized xylose in a concentrated exit stream;
   discharging the concentrated exit stream including the solubilized glucose or solubilized xylose for fermentation; and
   recirculating the permeate from the inorganic membrane element through the lignocellulosic biomass.

2. The pretreatment process of claim 1 wherein the pressurized solution is heated to between 170° C. and 230° C.

3. The pretreatment process of claim 1 wherein the pressurized solution is pressurized to between 200 psig and 550 psig relative to the permeate.

4. The pretreatment process of claim 1 wherein the porous support defines a thickness of between 1 mm and 5 mm.

5. The pretreatment process of claim 1 wherein the membrane element is tubular and defines a plurality of longitudinal channels therethrough.

6. The pretreatment process of claim 1 wherein the lignocellulosic biomass is suspended in a flow-through reactor.

7. The pretreatment process of claim 6 further including hydrolyzing the lignocellulosic biomass in the flow-through reactor.

8. The pretreatment process of claim 1 wherein the pressurized liquid includes water and does not generate products in the biomass suspension that are inhibitory to fermentation.

* * * * *